United States Patent
Hujzer et al.

[11] Patent Number: 5,824,915
[45] Date of Patent: Oct. 20, 1998

[54] VOLUMETRIC FLOW METER

[75] Inventors: Arie Hujzer; Andre H. Boer, both of Sliedrecht, Netherlands

[73] Assignee: Krohne A.G., Switzerland

[21] Appl. No.: 836,177

[22] PCT Filed: Aug. 21, 1996

[86] PCT No.: PCT/EP96/03670

§ 371 Date: Jul. 7, 1997

§ 102(e) Date: Jul. 7, 1997

[87] PCT Pub. No.: WO97/08516

PCT Pub. Date: Aug. 21, 1996

[30] Foreign Application Priority Data

Aug. 22, 1995 [DE] Germany ............... 195 30 807.7

[51] Int. Cl.$^6$ .................................................. G01F 01/66
[52] U.S. Cl. .................................. 73/861.27; 73/861.18; 73/644
[58] Field of Search ................. 73/861.26, 861.27, 73/861.28, 861.29, 861.31, 632, 644, 861.18

[56] References Cited

U.S. PATENT DOCUMENTS

| | | | |
|---|---|---|---|
| 3,925,692 | 12/1975 | Leschek et al. | 310/8.7 |
| 4,014,211 | 3/1977 | Araki et al. | 73/644 |
| 4,374,477 | 2/1983 | Kikuchi et al. | 73/861.27 |
| 4,505,160 | 3/1985 | Zacharias et al. | 73/861.18 |
| 4,783,997 | 11/1988 | Lynnworth | 73/644 |
| 4,948,552 | 8/1990 | Mollot et al. | 73/644 |
| 5,280,728 | 1/1994 | Sato et al. | 73/861.28 |

FOREIGN PATENT DOCUMENTS

| | | |
|---|---|---|
| 0 198 731 A2 | 10/1986 | European Pat. Off. . |
| 0 249 691 | 12/1987 | European Pat. Off. . |
| 61-93914 | 5/1986 | Japan . |

*Primary Examiner*—Ronald L. Biegel
*Attorney, Agent, or Firm*—Cesari and McKenna, LLP

[57] ABSTRACT

A volume flow meter for flowing media that works on the transit-time principle includes a conduit measurement section carrying the flowing medium, two ultrasonic transducers arranged on opposite ends of the conduit measurement section sending ultrasonic signals into the flowing medium and/or receiving them from the flowing medium and a control and evaluation circuit. The ultrasonic transducers send ultrasonic signals into the flowing medium via thermally insulating ultrasonic waveguides. The control and evaluation circuit determines the volume flow based on the difference between the total transit time of the ultrasonic signals between the ultrasonic transducers and the sum of the transit times of the ultrasonic signals in the ultrasonic waveguies.

3 Claims, 3 Drawing Sheets

VOLUMETRIC FLOW METER

BACKGROUND OF THE INVENTION

The invention concerns a volume flow meter for flowing media that works on the transit time principle, with a conduit measurement section, two ultrasonic transducers arranged at opposite ends of the conduit measurement section that send ultrasonic signals into the flowing medium and/or receive them from the flowing medium and a control and evaluation circuit, wherein the control and evaluation circuit measures the transit time of the ultrasonic signals between the ultrasonic transducers to determine the volume flow through the conduit measurement section.

Since the known volume flow meters on which the invention is based have proven very good when used in the industrial sector, many other applications have recently been developed for these volume flow meters, particularly applications in which the flowing medium has clearly high temperatures. Here, their use in the area of oil extraction is mentioned only as an example. Since piezo crystals are generally used as the basic component of the ultrasonic transducer in the known volume flow meters, the possibilities of using the known volume flow meters are limited to a temperature range up to 120° C., but at the most 150° C. At higher temperatures, the ultrasonic transducers regularly used are subject to problems or are completely dysfunctional.

SUMMARY OF THE INVENTION

The task of the invention is, therefore, to develop and design the known volume flow meters in such a way that they can be used even when the flowing medium is at high temperatures and in such a way that they have superior measurement precision.

The volume flow meter in the invention for flowing media that works on the transit time principle, in which the task introduced and described above is solved, is characterized by the fact that the ultrasonic transducers send ultrasonic signals into the flowing medium via thermally insulating ultrasonic waveguides. The invention guarantees that the high to very high temperatures in the flowing medium are far from being reached on the ultrasonic transducer because of the thermally insulating ultrasonic waveguide placed between the flowing medium and the ultrasonic transducers. In one suitable design of the thermally insulating ultrasonic waveguide, for example, temperatures of up to 1000° C. are possible for the flowing medium without affecting conventionally—and hence inexpensively—designed ultrasonic transducers.

One first advantageous embodiment of the invention of the volume flow meter is that the ultrasonic waveguide is designed in the form of a rod. The rod-shaped design of the ultrasonic waveguide guarantees that even materials with higher heat-conducting coefficients, but even better other material parameters, particularly with regard to the required ultrasonic waveguide properties, can be used as the starting material to produce ultrasonic waveguides.

A particularly big difference between the temperature of the flowing medium and the temperature of the ultrasonic transducer can be guaranteed in the volume flow meter according to the invention by the fact that a cooling device is provided to cool the ultrasonic waveguide. Here, both active cooling devices, like water or air cooling, and passive cooling devices are conceivable.

An especially advantageous design for the volume flow meter in the invention is one in which the ultrasonic waveguides have at least one cooling rib. This passive cooling device is particularly advantageous since it requires no other installation expense and is extremely trouble-free.

Finally, it has also proven particularly advantageous to produce the ultrasonic waveguides of stainless steel. Ultrasonic waveguides produced in this way are inexpensive, have a relatively low heat-conducting coefficient and have good ultrasonic wave-conduction properties.

The invention's design of the volume flow meter necessitates conversion of the method for determining volume flow according to the transit-time principle, which can be used in a volume flow meter designed according to the invention.

The method for determining volume flow according to the transit-time principle, with the help of a volume flow meter designed according to the invention, is advantageously designed so that the control and evaluation circuit determines the volume flow based on the difference between the total transit time of the ultrasonic signals between the ultrasonic transducers and the sum of the transit times of the ultrasonic signals in the ultrasonic waveguides. Not considering the transit times of the ultrasonic signals in the ultrasonic waveguides would result in a relatively large error in the measurement results for volume flow. This is avoided by the method of determining volume flow described.

The transit time for the ultrasonic signals in the ultrasonic waveguides can now be found, for example, as part of a calibration process and can be fed to the control and evaluation circuit as a fixed value. One particularly advantageous embodiment is the method whereby the control and evaluation circuit determines the transit time of the ultrasonic signals in the ultrasonic waveguides from the portions of the ultrasonic signals reflected on the ends of the ultrasonic waveguides facing the flowing medium. This guarantees that the actual, temperature-dependent transit time of the ultrasonic signals in the ultrasonic waveguides is always used for correction. Compared to finding the transit time of the ultrasonic signals in the ultrasonic waveguides only once, this step produces an improvement in measurement precision from approximately ±4% to approximately 0.2%.

Another increase in measurement precision is guaranteed by the fact that the temperature of the flowing medium is determined by the control and evaluation circuit from the transit time of the ultrasonic signals in the ultrasonic waveguides and by the fact that the result for volume flow is corrected by the control and evaluation circuit using the temperature of the flowing medium. Since the transit time of the ultrasound signals in the ultrasonic waveguides is a direct measure of the temperature of the ultrasonic waveguides, the temperature of the flowing medium can also be deduced from the transit time of the ultrasonic signals in the ultrasonic waveguides. The temperature of the flowing medium now has a major influence on the measurement precision of the volume flow meter. Depending on the temperature, for example, the pipeline diameter of the conduit measurement section changes. Since this is a volume flow meter and not a mass flow meter, an increase in the diameter of the conduit measurement section leads to a reduction in the measured velocity of the flowing medium, which, in turn, without correction produces too low a value for the volume flow. Due to the effect described, if there is an increase in the temperature of the flowing medium from 240° C. up to 260° C. without correction, there is an error of approximately 1.5%. With the correction described, this error falls to 0.1%.

BRIEF DESCRIPTION OF THE DRAWINGS

Now there are many ways of designing and developing the volume flow meter for flowing media in the invention that works on the transit-time principle and the method of determining volume flow by the transit-time principle using the volume flow meter in the invention. Please refer, on one hand, to the dependent patent claims and, on the other hand, to the description of the preferred examples of embodiment in connection with the drawings, in which:

DETAILED DESCRIPTION OF AN ILLUSTRATIVE EMBODIMENT

Figure 1:
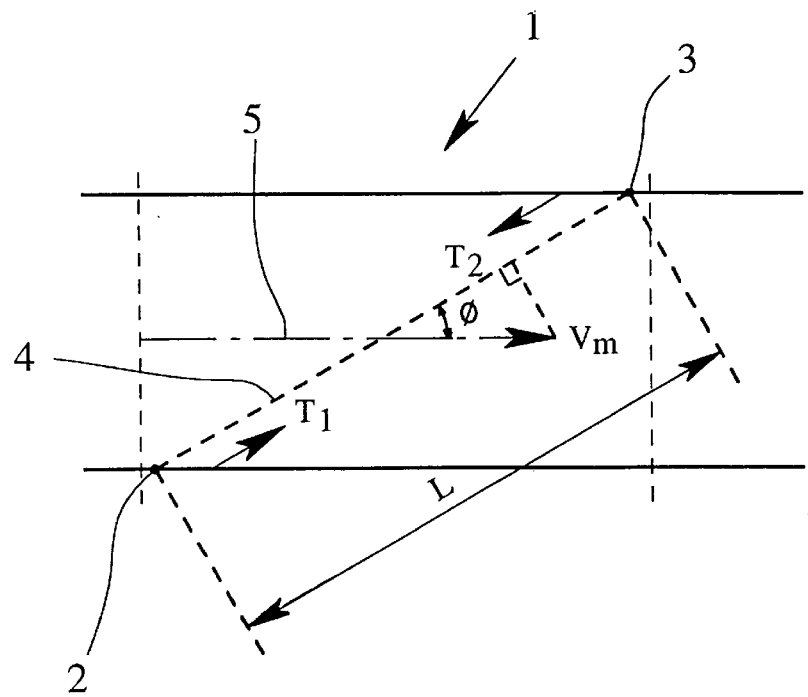
FIG. 1 is a schematic representation of a known volume flow meter for flowing media that works on the transit-time principle.

FIG. 1 shows a known volume flow meter for flowing media that works on the transit-time principle. The volume flow meter has a conduit measurement section 1 carrying the flowing medium. On opposite ends of the conduit measurement section 1, there are two ultrasonic transducers 2,3 sending ultrasonic signals into the flowing medium and/or receiving them from the flowing medium. FIG. 1 does not show the control and evaluation circuit that measures the transit time of the ultrasonic signals between the ultrasonic transducers 2,3 to determine the volume flow through the conduit measurement section 1.

The conduit measurement section 1 shown in FIG. 1 represents either an independent part within a conduit system, or it is made up of one part of an existing conduit system.

As shown in FIG. 1, known volume meters are generally designed in such a way that the measurement line 4 connecting the ultrasonic transducers 2, 3 cuts the longitudinal axis 5 of the conduit measurement section 1 at an angle ø. Under special circumstances, namely when the ultrasonic transducers 2,3 are arranged in curves in the conduit system on the longitudinal axis 5 of the conduit measurement section 1, the angle ø is up to 0°.

In order to guarantee an intensive ultrasonic signal at the receiving ultrasonic transducer 2,3, it makes sense for the ultrasonic transducers 2,3 to be aligned with one another.

Both ultrasonic transducers 2,3 are now controlled by the control and evaluation circuit in such a way that an ultrasonic transducer 2,3 sends out ultrasonic signals that are received by the other ultrasonic transducer 3,2. If the propagation speed $c_0$ of the ultrasonic signals in the flowing medium is not known, it is necessary for the ultrasonic transducers 2,3 to be controlled alternately as sender and receiver. The transmit times between the ultrasonic transducers 2,3 are thus:

$$T_1 = \frac{L}{V_1} = \frac{L}{c_o - V_m \cos\varphi} \qquad \text{Equation 1}$$

$$T_2 = \frac{L}{V_2} = \frac{L}{c_o + V_m \cos\varphi} \qquad \text{Equation 2}$$

In these equations, L stands for the distance between the two transducers 2,3 and $V_m$ is the average velocity of the flowing medium in the conduit measurement section 1. Because the average velocity $V_m$ of the flowing medium is different from zero, the transit time $T_1$ of the ultrasonic signal from ultrasonic transducer 2 to ultrasonic transducer 3 is smaller than the reverse, i.e., the transit time $T_2$ from ultrasonic transducer 3 to ultrasonic transducer 2.

Now, from equations 1 and 2, with known transit times $T_1$ and $T_2$, the unknown variables $c_0$ and $V_m$ can be determined. The volume flow through the conduit measurement section 1 that is being found then comes from $V_m$ in connection with the cross section of the conduit measurement section 1.

The working method described up to this point is for known volume flow meters.

Figure 2:
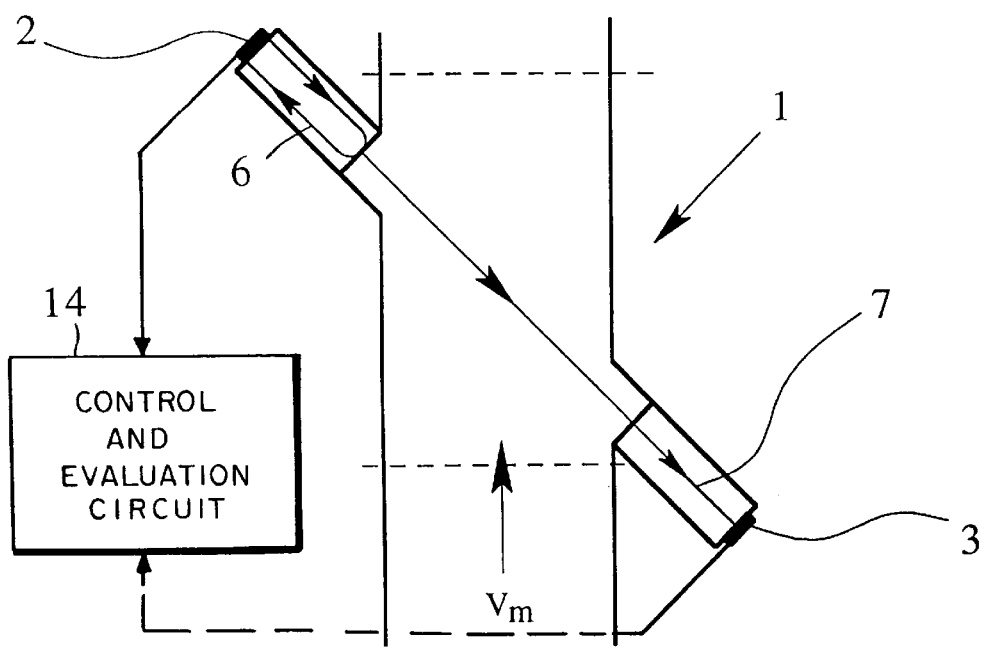
FIG. 2 is a schematic representation of a volume flow meter designed according to the invention for flowing media that works on the transit-time principle.

FIG. 2 of the drawings now shows a volume flow meter designed according to the invention. This volume flow meter differs from the known one in that the ultrasonic transducers 2,3 are not placed in direct contact with the flowing medium. FIG. 2 shows schematically that the ultrasonic transducers 2,3 send ultrasonic signals via thermally insulating ultrasonic waveguides 6,7 into the flowing medium. The synopsis in FIGS. 1 and 2 and Equations 1 and 2 shows the need to consider the transit times of the ultrasonic signals in the ultrasonic waveguides 6,7 before determining volume flow by means of a control and evaluation circuit 14. FIG. 2 of the drawings also shows for the ultrasonic waveguide 6 that part of the ultrasonic signal is reflected on the end of the ultrasonic waveguides 6,7 facing the flowing medium. This part can be changed by special designs of the ultrasonic waveguide 6,7.

Figure 3:
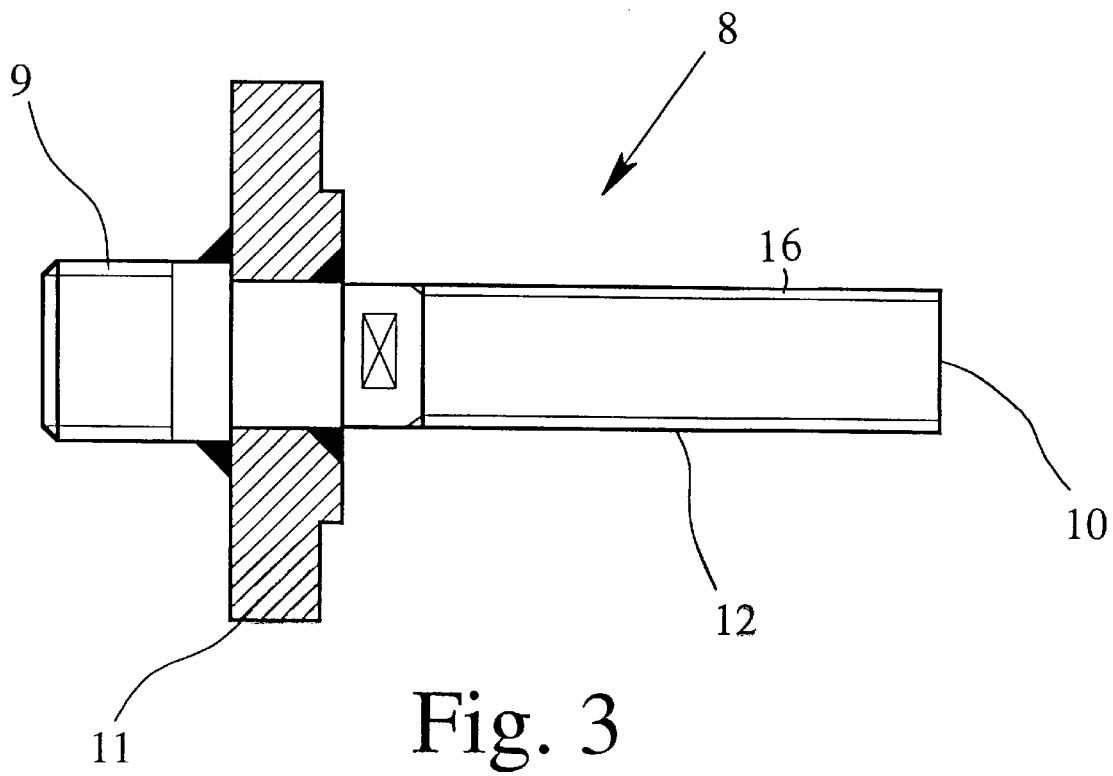
FIG. 3 is a cross section through one example of embodiment of an ultrasonic waveguide provided according to the invention.

FIG. 3 shows a cross section through an example of embodiment of a rod-shaped ultrasonic waveguide 8. This rod-shaped ultrasonic waveguide 8 is connected on the first end 9 to the flowing medium and on the second end 10 is in contact with one of the ultrasonic transducers 2,3. The advantage of the rod-shaped ultrasonic waveguide 8 in the invention is due to the thermally insulating properties of the insulating section 12 arranged between the second end 10 and the mounting flange 11. This insulating section 12 can, for example, also be provided with one or more cooling ribs 16 and is preferably made of stainless steel—but ceramic or plastic are also conceivable, for example, as a starting material for the ultrasonic waveguide 8.

Figure 4:
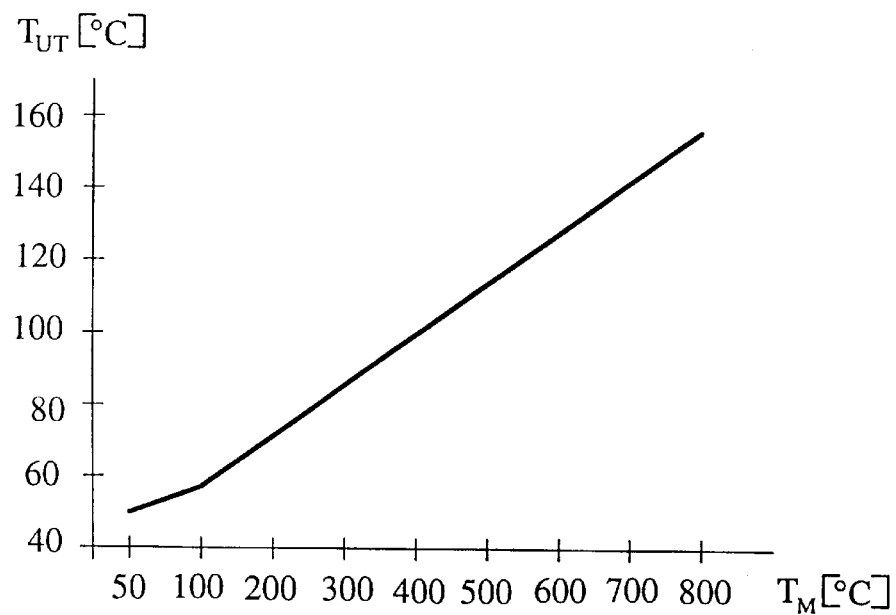
FIG. 4 is a graphical diagram which shows the dependence of the temperature of the ultrasonic transducer on the temperature of the flowing medium in a volume flow meter designed according to the invention.

FIG. 4 is a diagram showing the dependence of the temperature $T_{UT}$ of one of the ultrasonic transducers 2,3 on the temperature $T_M$ of the flowing medium. The diagram in FIG. 4 was recorded at an ambient temperature of 50° C. and a length of 15 cm for the insulating section 12. It is clear that temperatures up to 800° C. for the flowing medium are allowed without affecting or damaging one of the ultrasonic transducers 2,3.

Figure 5:
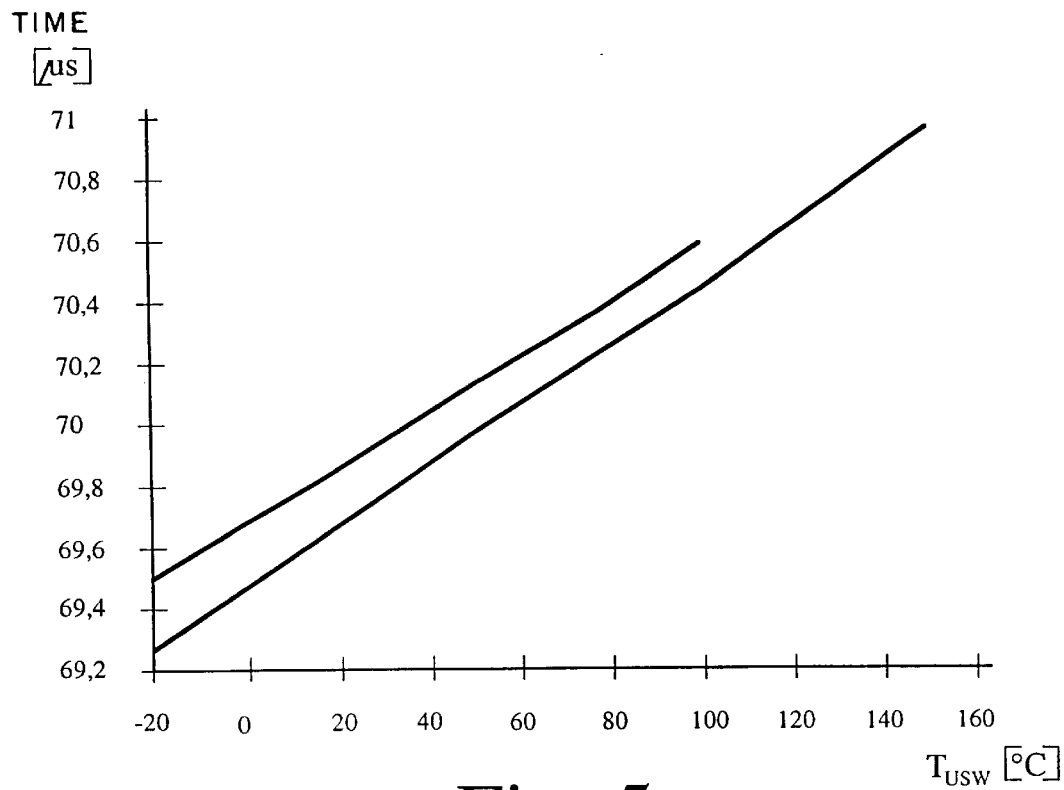
FIG. 5 is a similar diagram that shows the dependence of the transit times of an ultrasonic signal in an ultrasonic waveguides on the temperature in question.

The dependence of the transit times of the ultrasonic signals in the ultrasonic waveguides 6,7 on the temperature in question $T_{USW}$ of the ultrasonic waveguides 6,7 is shown in FIG. 5. The straight line on top shows the dependence of the transit time of the portions of the ultrasonic signals reflecting on the ends of the ultrasonic waveguides 6,7 facing the flowing medium on the temperature of the ultrasonic waveguides 6,7. The lower straight line in FIG. 5 shows the dependence of the sums of the transit times of an ultrasonic signal in both ultrasonic waveguides 6,7 depending on their temperature. FIG. 5 shows clearly that the determination of the transit time of the ultrasonic signals in the ultrasonic waveguides 6,8 from the portions of the ultrasonic signals reflecting on the ends of the ultrasonic waveguides 6,7 facing the flowing medium allows a very good correction of the sum of the temperature-dependent transit times of the ultrasonic signals in the individual ultrasonic waveguides 6,7.

Figure 6:
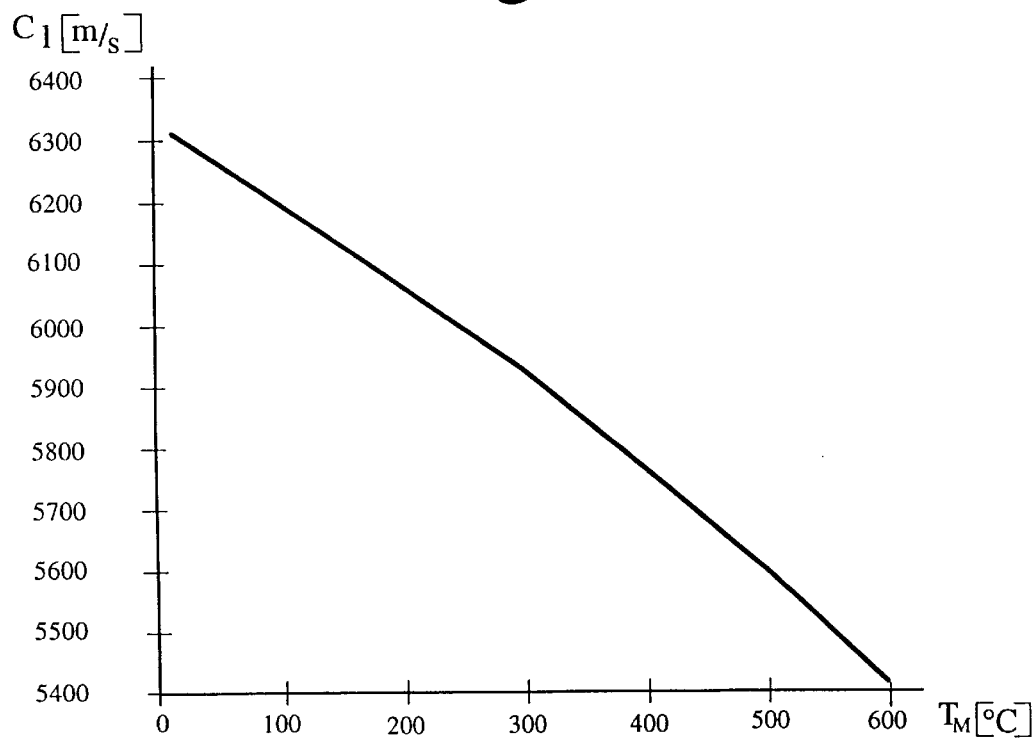
FIG. 6 is a graphical diagram that shows the dependence of the propagation speed of an ultrasonic waveguide on the temperature of the flowing medium.

FIG. 6 shows the dependence of the propagation speed $c_1$ of the ultrasonic signals in the ultrasonic waveguides 6,7 on the temperature $T_M$ of the flowing medium. Here it is clear that the temperature of the flowing medium $T_M$ can be determined with no problem from the transit time of the ultrasonic signals in the ultrasonic waveguides 6,7 and thus can be used to correct the value for the volume flow. This correction can be made, for example, by determining the current diameter of the conduit measurement section 1 based on a known diameter of the conduit measurement section 1 at a predetermined temperature and the temperature of the flowing medium, found as explained, using material constants for the material of the conduit measurement section 1.

What is claimed is:

1. A method of determining volume flow according to the transit-time principle, using a volume flow meter with a conduit measurement section carrying the flowing medium, two ultrasonic transducers arranged on opposite ends of the conduit measurement section sending ultrasonic signals into the flowing medium and/or receiving them from the flowing medium and a control and evaluation circuit and wherein the ultrasonic transducers send ultrasonic signals into the flowing medium via ultrasonic waveguides and the control and evaluation circuit measures the transit time of the ultrasonic signals between the ultrasonic transducers and the transit time of the ultrasonic signals in the ultrasonic waveguides to determine the volume flow through the conduit measurement section, the improvement wherein the ultrasonic waveguides are in contact with the flowing medium and are thermally insulating and the control and evaluation circuit determines the volume flow based on the difference between the transit time of the ultrasonic signals between the ultrasonic transducers and the sum of the transit times of the ultrasonic signals in the ultrasonic waveguides.

2. The method of claim 1 wherein the control and evaluation circuit determines the transit time of the ultrasonic signals in the ultrasonic waveguides from the parts of the ultrasonic signals reflecting on the ends of the ultrasonic waveguides facing the flowing medium.

3. The method of claim 1 or 2 wherein the control and evaluation circuit determines the temperature of the flowing medium from the transit time of the ultrasonic signals in the ultrasonic waveguides and corrects the volume flow according to the determined temperature of the flowing medium.

* * * * *

UNITED STATES PATENT AND TRADEMARK OFFICE
CERTIFICATE OF CORRECTION

PATENT NO.    : 5,824,915
DATED         : October 20, 1998
INVENTOR(S)   : Arie Hujzer et al.

It is certified that error appears in the above-identified patent and that said Letters Patent is hereby corrected as shown below:

<u>Title page,</u>
Item [22], please correct the filing date to read -- July 2, 1997 --

Signed and Sealed this

First Day of April, 2003

JAMES E. ROGAN
*Director of the United States Patent and Trademark Office*